US00PP16300P3

(12) United States Plant Patent
Austin

(10) Patent No.: US PP16,300 P3
(45) Date of Patent: Feb. 28, 2006

(54) SHRUB ROSE PLANT NAMED 'AUSPISHUS'

(50) Latin Name: *Rosa hybrida*
Varietal Denomination: AUSpishus

(75) Inventor: David C. H. Austin, Wolverhampton (GB)

(73) Assignee: David Austin Roses Limited, Albrighton (GB)

( * ) Notice: Subject to any disclaimer, the term of this patent is extended or adjusted under 35 U.S.C. 154(b) by 80 days.

(21) Appl. No.: 10/945,778

(22) Filed: Sep. 20, 2004

(65) Prior Publication Data

US 2005/0183178 P1 Aug. 18, 2005

(51) Int. Cl.
*A01H 5/00* (2006.01)

(52) U.S. Cl. ..... Plt./107

(58) Field of Classification Search ..... Plt./107
See application file for complete search history.

*Primary Examiner*—Anne Marie Grunberg
*Assistant Examiner*—Annette H Para
(74) *Attorney, Agent, or Firm*—Klarquist Sparkman LLP

(57) ABSTRACT

Shrub rose plant having deep pink blooms of the hybrid tea type, long arching growth, strong Tea Rose fragrance and vigorous, branching growth.

1 Drawing Sheet

Genus and species: *Rosa hybrida.*
Variety denomination: 'AUSpishus'.

ORIGIN OF THE INVENTION

The present invention relates to a new and distinct variety of a shrub rose plant named 'AUSpishus' which was originated by me by crossing the variety 'AUSgold' (Golden Celebration), U.S. Plant Pat. No. 8,688, with an unnamed, unpatented seedling.

BACKGROUND OF THE INVENTION

The primary objective of this breeding was to produce a new rose variety having long arching growth, bearing long elegant buds which open into rosette shaped blooms of deep pink, paling at the edges.

BRIEF SUMMARY OF THE INVENTION

The objective was substantially achieved, along with other desirable improvements, as evidenced by the following unique combination of characteristics that are outstanding in the new variety and that distinguish it from its parents, as well as from all other varieties of which I am aware:

1. Deep pink blooms of the hybrid tea type.
2. Long, arching growth.
3. Strong, Tea Rose fragrance.
4. Vigorous, branching growth.

Asexual reproduction of this new variety by budding, as performed at Albrighton, England, shows that the foregoing and all other characteristics and distinctions come true to form and are established and transmitted through succeeding propagations.

COMPARISON WITH PARENTS

'AUSgold' (Golden Celebration)has large cupped golden-yellow flowers compared with the rosette shaped deep pink flowers of 'AUSpishus'. The unnamed pollen parent has a cupped bloom compared to the rosette bloom of 'AUSpishus'.

COMPARISON WITH SIMILAR VARIETY

'AUSsaucer' (U.S. Plant Pat. No. 8,680) has apricot blooms with an Old Rose fragrance and greater petalage than the pink blooms of 'AUSpishus' whose fragrance is of Tea Rose character.

BRIEF DESCRIPTION OF THE ILLUSTRATION

The accompanying illustration shows typical specimens of the vegetative growth and flowers of this new variety in different stages of development, depicted in color as nearly true as it is reasonably possible to make the same in a color illustration of this character.

DETAILED BOTANICAL DESCRIPTION

The following is a detailed description of my new rose cultivar with color descriptions using terminology in accordance with The Royal Horticultural Society (London) Colour Chart (2001), except where ordinary dictionary significance of color is indicated.

Parentage:
*Seed parent.*—'AUSgold' (U.S. Plant Pat. No. 8,688).
*Pollen parent.*—Unnamed Seedling. (Unpatented).

FLOWER

Observations made from plants commencing at one year of age grown in a garden environment at Albrighton, England.

Blooming habit: Recurrent.
Bud:
*Size.*—About 2.9 cm long and 2 cm in diameter when the petals start to unfurl.
*Form.*—The bud form is pointed ovoid.

*Color.*—When sepals first divide, bud color is Yellow-Green Group 144B. When half blown, the upper sides of the petals are Red Group 37D; and the lower sides of the petals are Orange Group 27B.

*Sepals.*—Color: Upper surface: Yellow-Green Group 144A. Lower surface: Yellow-Green Group 144A. Length: 2.4 cm. Width: 0.8 cm. Shape: Awl-shaped. Surface texture: Upper surface: Pubescent. Lower surface: Smooth. There are three lightly appendaged sepals. There are three unappendaged sepals with smooth edges.

*Receptacle.*—Color: Yellow-Green Group 144A. Shape: Campanulate. Size: Medium, about 1.1 cm long×1.2 cm wide. Surface: Smooth.

*Peduncle.*—Length: Medium, averaging about 6 cm. Surface: Smooth. Color: Yellow-Green Group 144B. Strength: Strong.

Bloom:

*Size.*—Large. Average open diameter is about 8.1 cm.

*Borne.*—Singly and in flat clusters of up to four blooms.

*Stems.*—Strength: Normal. Average length is about 62 cm with a diameter of 0.8 cm. Internode distance about 6 cm.

*Form.*—When first open: High centered. Permanence: Outer petals curl back.

*Petalage.*—Number of petals under normal conditions: 76.

*Color.*—The upper sides of the petals are Red-Purple Group 62B at the outer part and Yellow Group 10D towards the base. The reverse sides of the petals are Yellow Group 11C at the outer part and Yellow Group 10C towards the base. The base of each petal is Yellow Group 10D. The major color on the upper side is Red-Purple Group 62B.

*Variegations.*—None.

*Discoloration.*—The general tonality at the end of the first day: Red-Purple Group 62B. At the end of the third day: Fading to Purple Group 75D.

*Fragrance.*—Strong, Tea Rose.

Petals:

*Texture.*—Satiny.

*Size.*—Width: 5 cm. Length: 5 cm.

*Surface.*—Smooth.

*Shape.*—Round. Margin: Reflexing and undulating. Apex Shape: Orbicular, some notched. Base Shape: Pointed.

*Form.*—Incurved, with heavily reflexing margin.

*Arrangement.*—Quartered.

*Petaloids.*—Number: 7. Color: Red-Purple Group 61D.

*Persistence.*—Petals hang on and dry.

*Lastingness.*—On the plant: Long (about 5 days). As a cut flower: Fair (about 3 days).

Reproductive parts:

*Stamens.*—Number: 70. Length: 13 mm. Anthers: Length: 3 mm. Color: Yellow-Orange Group 17A. Arrangement: Mixed with petaloids. Filaments: Color: Yellow-Orange Group 17A. Length: 10 mm. Pollen: Color: Yellow-Orange Group 17B.

*Pistils.*—Number: 50. Length: 5 mm. Styles: Color: Red Group 49D. Length: 4 mm. Stigmas: Color: Yellow Group 10A. Length: 1 mm. Hips: None observed.

PLANT

*Form.*—Shrub.

*Growth.*—Vigorous, branching.

*Age at maturity.*—Two years.

*Mature plant.*—Height: 120 cm. Width: 100 cm.

*Rootstock.*—Dr. Huey in the United States. *Rosa dumetorum* 'Laxa' for the observed plants in the United Kingdom.

Foliage: Number of leaflets on normal mid-stem leaves: 5.

*Size.*—Large. About 13.5 cm long×10 cm wide.

*Quantity.*—Average number per flowering stem: 7.

*Color.*—New foliage: Upper side: Yellow-Green Group 146A. Lower side: Greyed-Orange Group 176B. Old foliage: Upper side: Yellow-Green Group 147A. Lower side: Yellow-Green Group 147B.

Leaflets:

*Size.*—About 5.7 cm long×4.4 cm wide.

*Shape.*—Pointed oval.

*Base shape.*—Obtuse.

*Apex shape.*—Rotundate.

*Texture.*—Leathery.

*Edge.*—Serrated.

*Serrations.*—Small.

*Petiole.*—Color: Green Group 137D.

*Petiole rachis.*—Color: Green Group 143C. Underside: Prickles.

*Auricle shape.*—Awl-shaped.

*Stipules.*—Length: 3.4 cm; serrated.

*Disease resistance.*—Resistant to both powdery and downy mildew, blackspot and rust under normal growing conditions.

*Pest resistance.*—Not tested.

*Vein color.*—Yellow-Green Group 146B.

*Venation pattern.*—Net-veined.

Wood:

*New wood.*—Color: Greyed-Orange Group 166A. Bark: Smooth.

*Old wood.*—Color: Yellow-Green Group 146A. Bark: Smooth.

Prickles:

*Quantity.*—On main canes from base: 22 per 30 cm per stem length. On laterals from main canes: 15 per 30 cm per stem length.

*Form.*—Hooked downward.

*Length.*—1.2 cm.

*Color when young.*—Green Group 143C.

*Color when mature.*—Greyed-Red Group 178B.

Small prickles:

*Quantity.*—On main stalks: 3 per 30 cm length of stem. On laterals: None observed.

*Color.*—When young: Greyed-Purple Group 183A. When mature: Greyed-Orange Group 172B.

Winter hardiness: Not tested.

I claim:

1. A new and distinct variety of rose plant of the shrub class, substantially as herein shown and described, characterized particularly by its deep pink blooms of the hybrid tea type, long arching growth, strong Tea Rose fragrance and vigorous, branching growth.

* * * * *

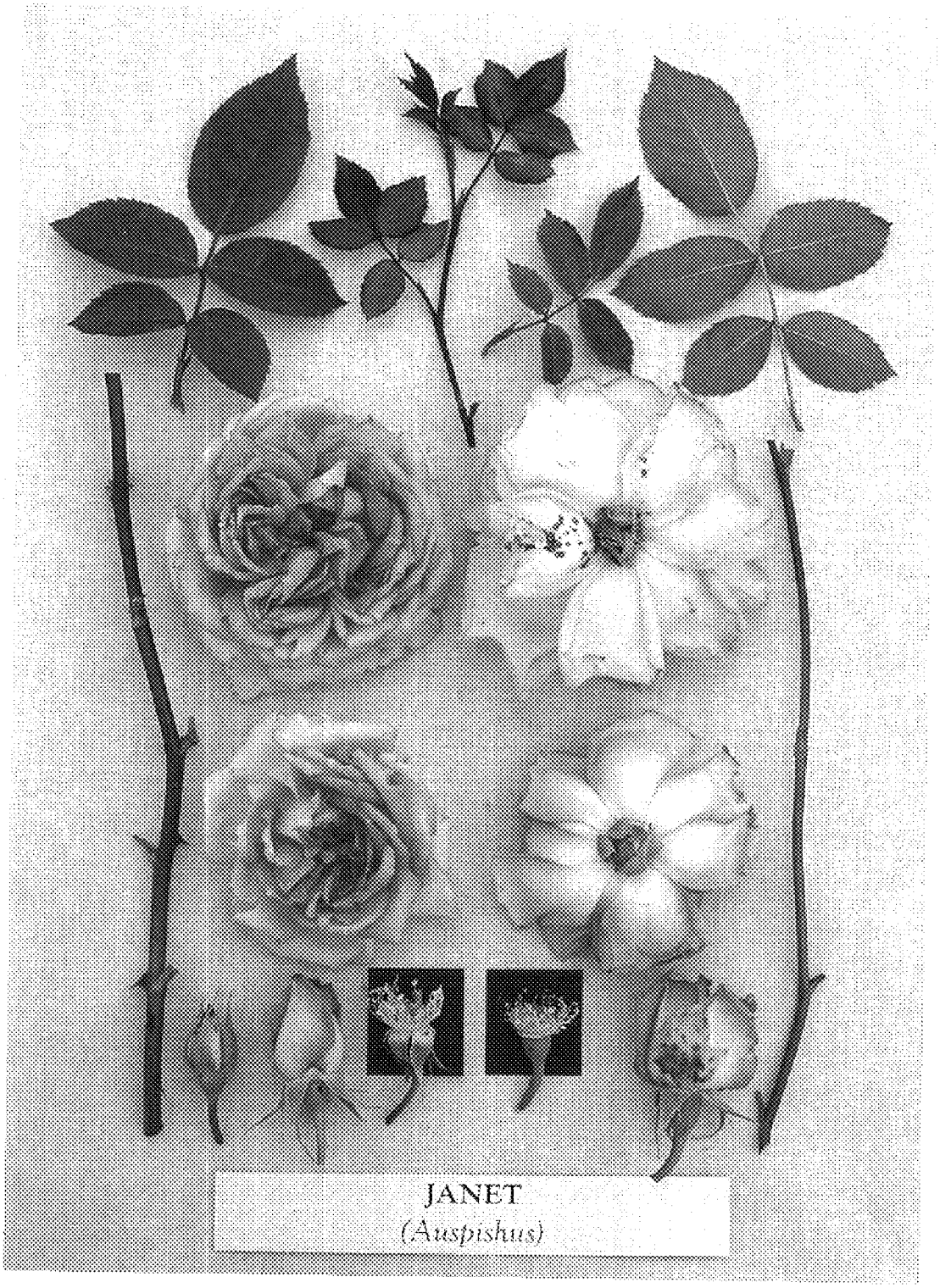
JANET
(Auspishus)